US009331113B2

(12) United States Patent
Ozcan et al.

(10) Patent No.: US 9,331,113 B2
(45) Date of Patent: May 3, 2016

(54) WIDE-FIELD LENSLESS FLUORESCENT IMAGING ON A CHIP

(75) Inventors: Aydogan Ozcan, Los Angeles, CA (US); Ahmet F. Coskun, Los Angeles, CA (US); Ikbal Sencan, Los Angeles, CA (US); Ting-Wei Su, Los Angeles, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 630 days.

(21) Appl. No.: 13/695,267
(22) PCT Filed: Apr. 25, 2011
(86) PCT No.: PCT/US2011/033819
§ 371 (c)(1), (2), (4) Date: Dec. 27, 2012
(87) PCT Pub. No.: WO2011/139641
PCT Pub. Date: Nov. 10, 2011

(65) Prior Publication Data
US 2013/0092821 A1 Apr. 18, 2013

Related U.S. Application Data
(60) Provisional application No. 61/330,799, filed on May 3, 2010, provisional application No. 61/430,449, filed on Jan. 6, 2011.

(51) Int. Cl.
*G01J 1/04* (2006.01)
*H01J 3/14* (2006.01)
(Continued)

(52) U.S. Cl.
CPC .......... *H01L 27/14625* (2013.01); *G01N 21/64* (2013.01); *G01N 21/648* (2013.01); *G01N 21/6456* (2013.01); *G01N 2021/6484* (2013.01); *G01N 2201/0833* (2013.01)

(58) Field of Classification Search
CPC ................ G01N 2021/392; G01N 2021/393; G01N 21/552; G01N 21/553; G01N 21/62; G01N 21/63

USPC ............ 356/417, 135, 136; 250/216, 227.11, 250/203.3, 227.2, 227.24, 306, 307, 250/573–576, 428, 458.1, 432 R, 459.1, 250/462.1, 483.1, 484.2, 484.4; 359/368, 359/642, 665, 831
See application file for complete search history.

(56) References Cited

U.S. PATENT DOCUMENTS 5,633,724 A * 5/1997 King et al. ..................... 356/445
6,646,272 B2 * 11/2003 Rushbrooke et al. ...... 250/461.1
(Continued)

FOREIGN PATENT DOCUMENTS

EP 1674852 A1 6/2006
JP 2002-502495 A 1/2002
(Continued)

OTHER PUBLICATIONS

PCT International Search Report for PCT/US2011/033819, Applicant: The Regents of the University of California, Form PCT/ISA/210 and 220, dated Dec. 16, 2011 (5pages).
(Continued)

*Primary Examiner* — Pascal M Bui Pho
(74) *Attorney, Agent, or Firm* — Vista IP Law Group LLP

(57) ABSTRACT

An imaging device uses a fiber optic faceplate (FOF) with a compressive sampling algorithm for the fluorescent imaging of a sample over an large field-of-view without the need for any lenses or mechanical scanning. The imaging device includes a sample holder configured to hold a sample and a prism or hemispherical glass surface disposed adjacent the sample holder on a side opposite the lower surface of the sample holder. A light source is configured to illuminate the sample via the prism or the hemispherical surface, wherein substantially all of the light is subject to total internal reflection at the lower surface of the sample holder. The FOF is disposed adjacent to the lower surface of the sample holder, the fiber optic array having an input side and an output side. The device includes an imaging sensor array disposed adjacent to the output side of the fiber optic array.

9 Claims, 13 Drawing Sheets

(51) Int. Cl.
*H01L 27/00* (2006.01)
*H01L 27/146* (2006.01)
*G01N 21/64* (2006.01)

(56) References Cited

U.S. PATENT DOCUMENTS

| | | | |
|---|---|---|---|
| 7,033,542 B2* | 4/2006 | Archibald et al. | 422/82.09 |
| 7,817,278 B2* | 10/2010 | VanWiggeren | G01N 21/553 |
| | | | 356/445 |
| 2002/0076729 A1 | 6/2002 | Meyer et al. | |
| 2008/0241866 A1 | 10/2008 | Korlach et al. | |
| 2009/0051766 A1* | 2/2009 | Shimbo | H04N 7/185 |
| | | | 348/143 |
| 2010/0144053 A1* | 6/2010 | Haushalter et al. | 436/164 |

FOREIGN PATENT DOCUMENTS

| | | |
|---|---|---|
| JP | 2008191054 A | 8/2008 |
| WO | WO 98/52023 A1 | 11/1998 |
| WO | WO 2008/140758 A1 | 11/2008 |
| WO | WO 2011/049965 A1 | 4/2011 |

OTHER PUBLICATIONS

PCT Written Opinion of the International Search Authority for PCT/US2011/033819, Applicant: The Regents of the University of California, Form PCT/ISA/237, dated Dec. 16, 2011 (3pages).

Hardie et al., Joint MAP Registration and High-Resolution Image Estimation Using a Sequence of Undersampled Images, IEEE, vol. 6 No. 12, Dec. 1997.

Ozcan et al., Ultra wide-filed lens-free monitoring of cells on-chip, Lab on Chip 8, 89-106, Nov. 1, 2007.

Ozcan et al., Lens-free On-Chip Cytometry for wireless Health Diagnosis, IEEE LEOS Newsletter, Oct. 2008.

Seo et al., Lensfree On-chip Cytometry Using Tunable Monochromatic Illumination and Digital Noise Reduction, Multi-color LUCAS, Sep. 2008.

Su et al., Towards Wireless Health: Lensless On-Chip Cytometry, Biophotonics, Dec. 2008.

Su et al., High-Throughput Lensfree Imaging and Characterization of Heterogeneous Cell Solution on a Chip, Biotechnology and Bioengineering, Sep. 8, 2008.

Isikman et al., Lensfree Cell Holography on a Chip: From Holographic Cell Signatures to Microscopic Reconstruction, LEOS Annual Meeting Conf. Proceedings, Oct. 2009.

Brady, David J. et al., Compressive Holography, Opt. Express 17, 13040-13049 (2009).

Coskun, Ahmet F. et al., Wide field-of-view lens-free fluorescent imaging on a chip, Lab Chip, 2010,10, 824-827 DOI: 10.1039/B926561A.

Denis, Loid et al., Inline hologram reconstruction with sparsity constraints, Opt. Lett. 34, 3475-3477 (2009).

Kim, Seung-Jean et al., An Interior-Point Method for Large-Scale l1-Regularized Least Squares, IEEE Journal on Selected Topics in Signal Processing, 1,4, 606-617, (2007).

Rust, Michael J. et al., Sub-diffraction-limit imaging by stochastic optical reconstruction microscopy (STORM) Nat. Methods 3: 793-796 (2006).

Seo, Sungkyu et al., Lensfree holographic imaging for on-chip cytometry and diagnostics, Lab on a Chip 9(6), 777-787 (2009).

PCT International Preliminary Report on Patentability (Chapter I of the Patent Cooperation Treaty) for PCT/US2011/033819, Applicant: The Regents of the University of California, Form PCT/IB/326 and 373, dated Nov. 15, 2012 (5pages).

Office Action draft dated Jan. 26, 2015 in Japanese Patent Application No. 2013-509110 (5pages), English translations prepared by Kita-Aoyama International Patent Bureau (4pages).

Mudanyali et al., Lensless On-chip Imaging of Cells Provides a New Tool for High-throughput Cell-Biology and Medical Diagostics, Journal of Visualized Experiments, Dec. 14, 2009.

* cited by examiner

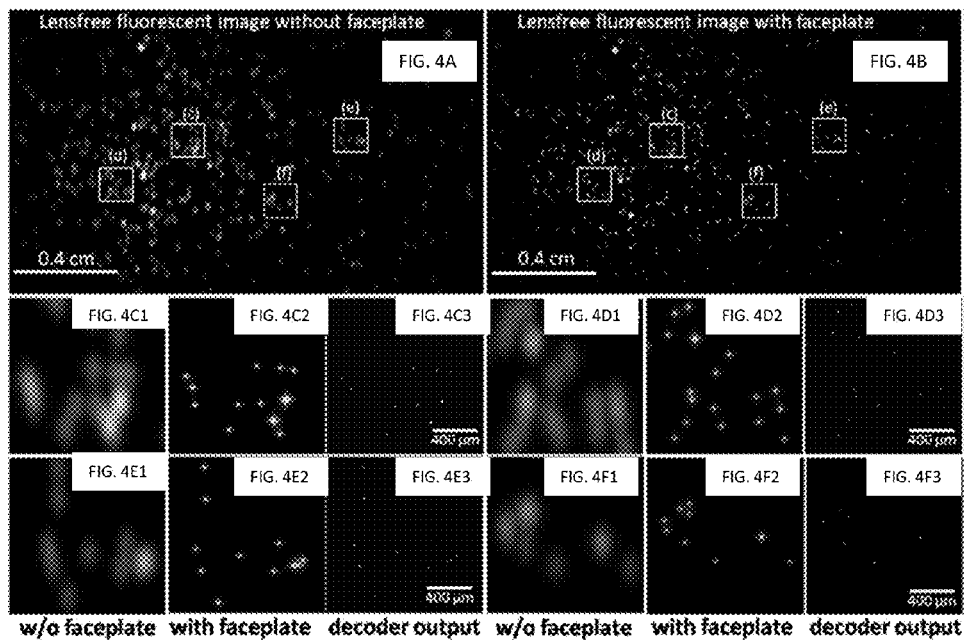

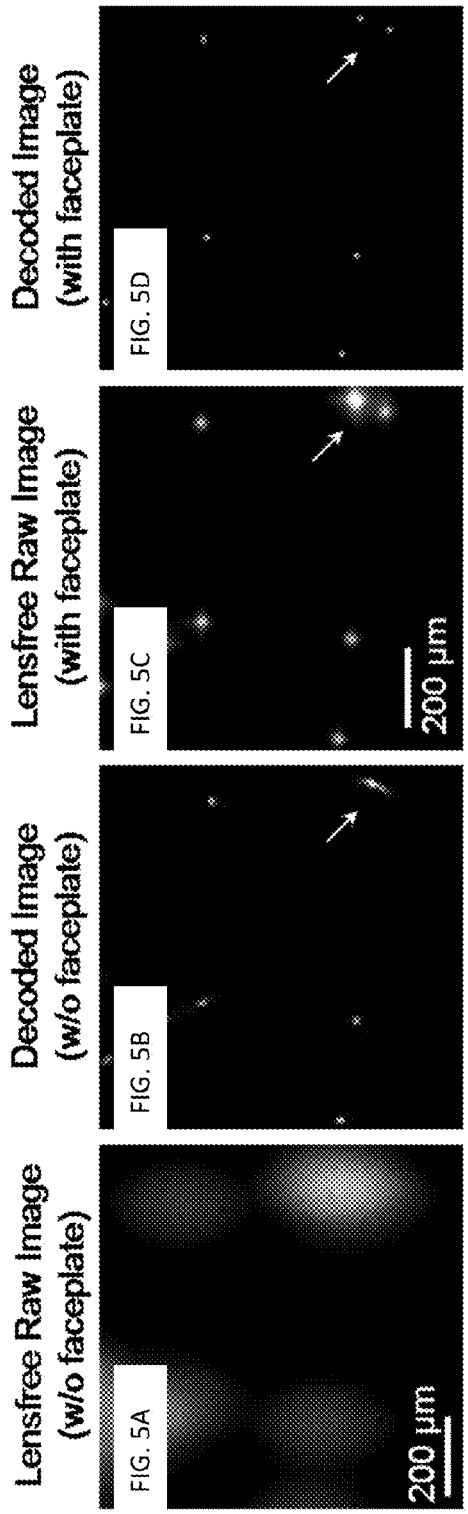

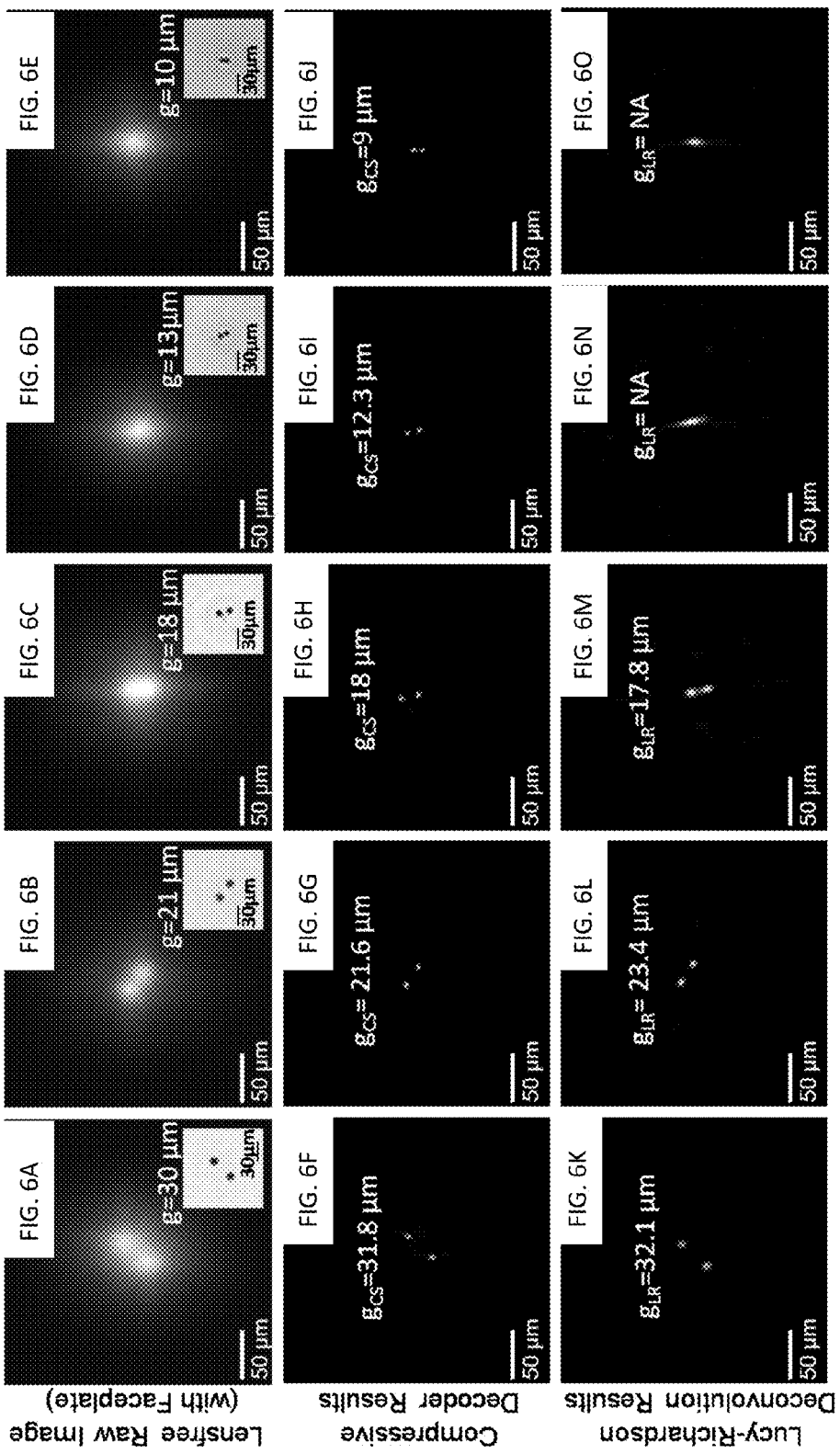

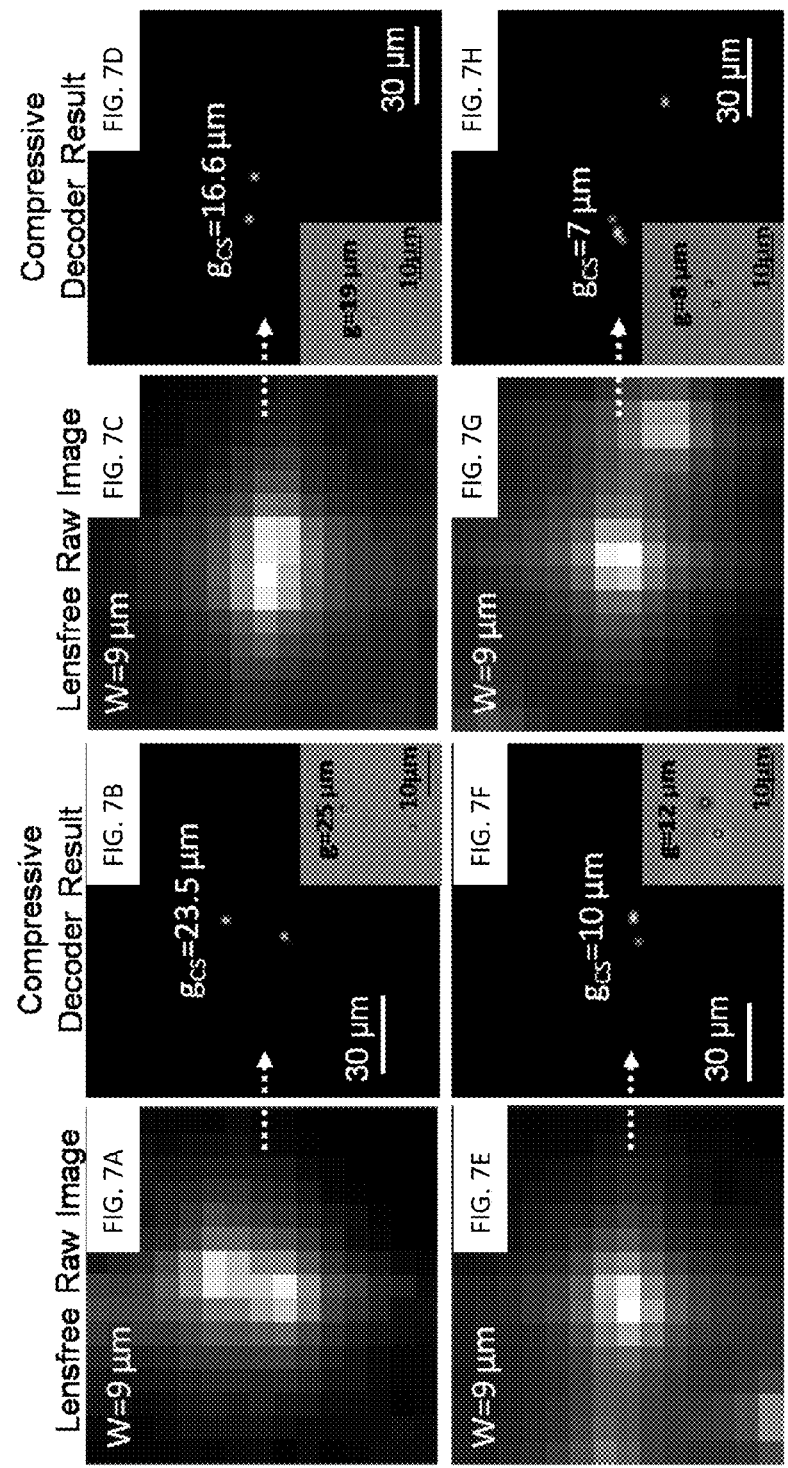

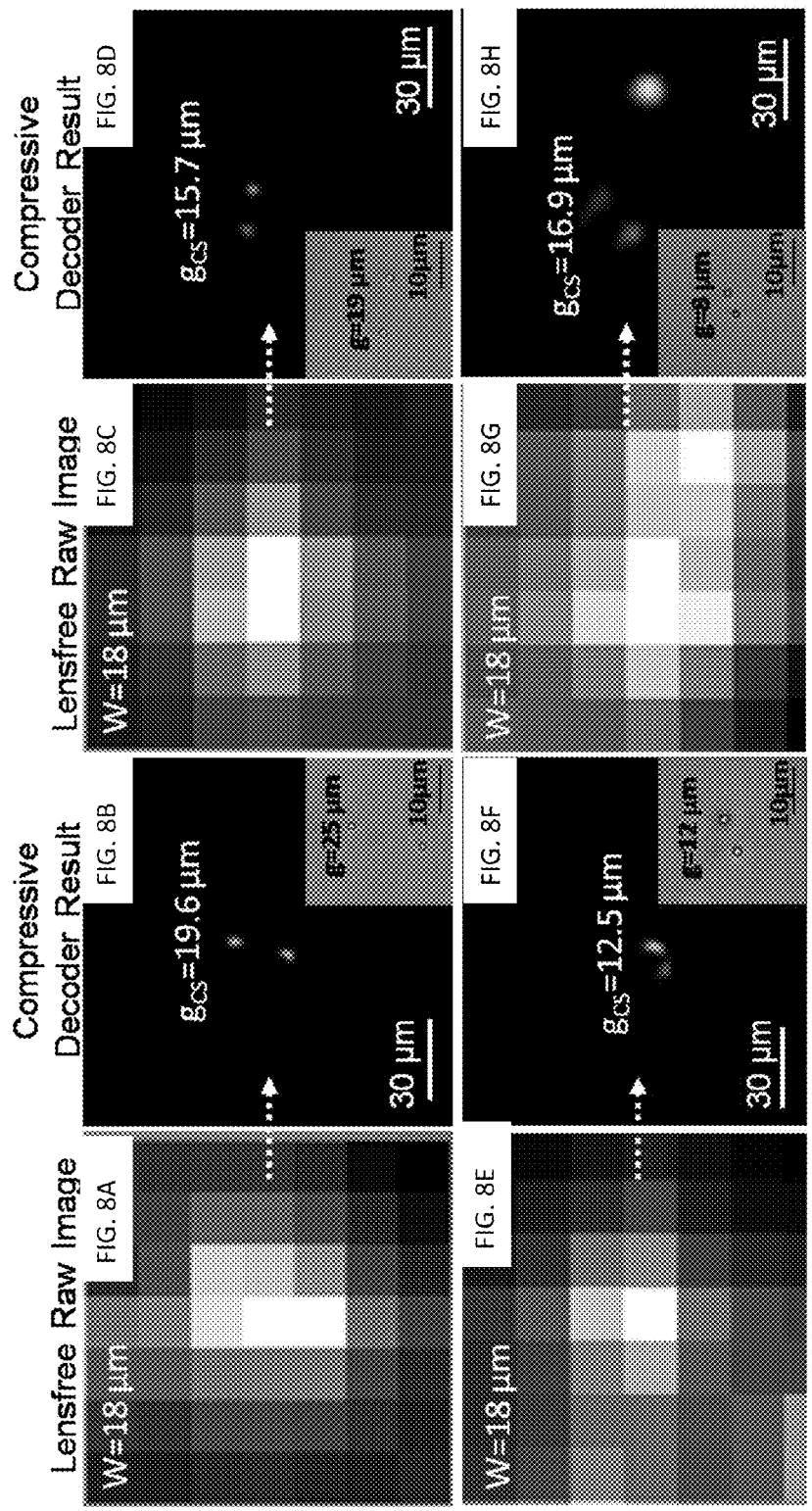

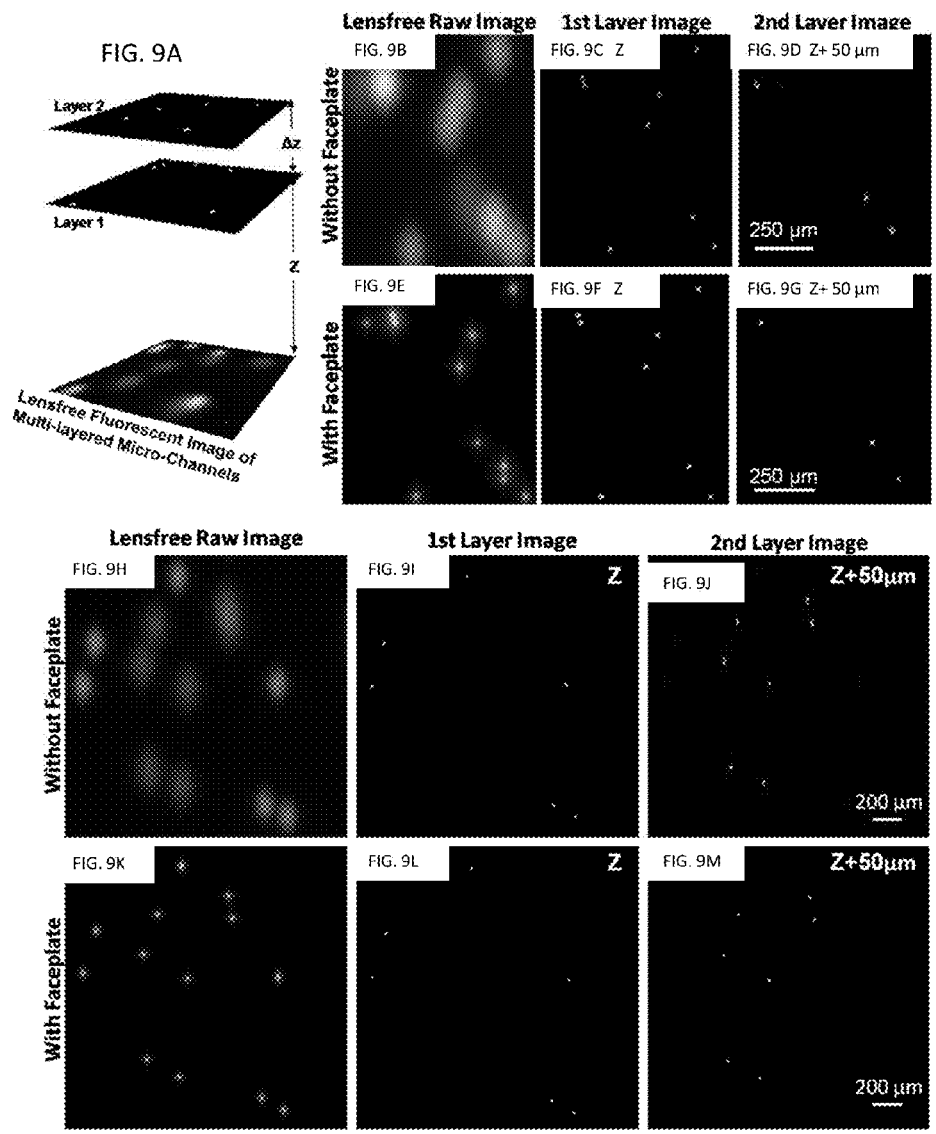

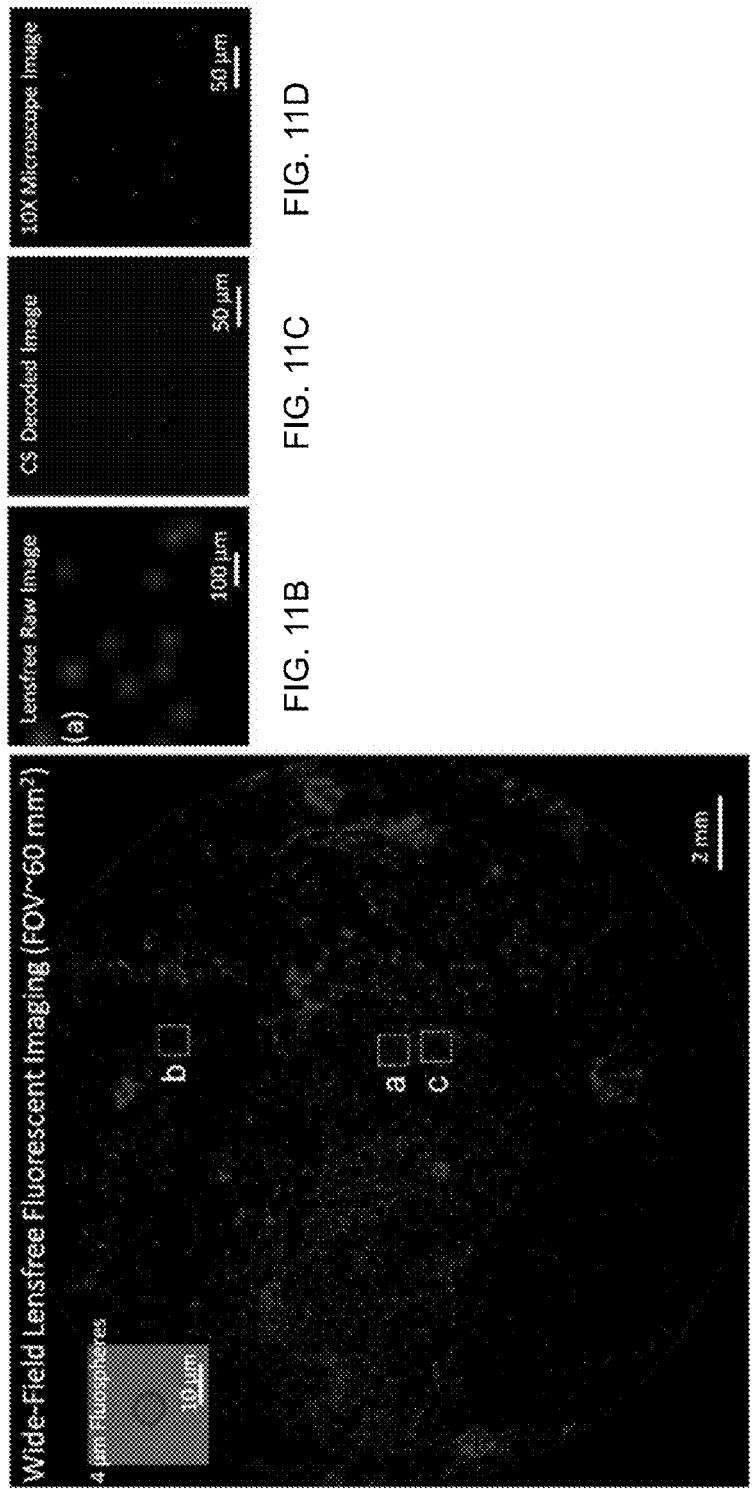

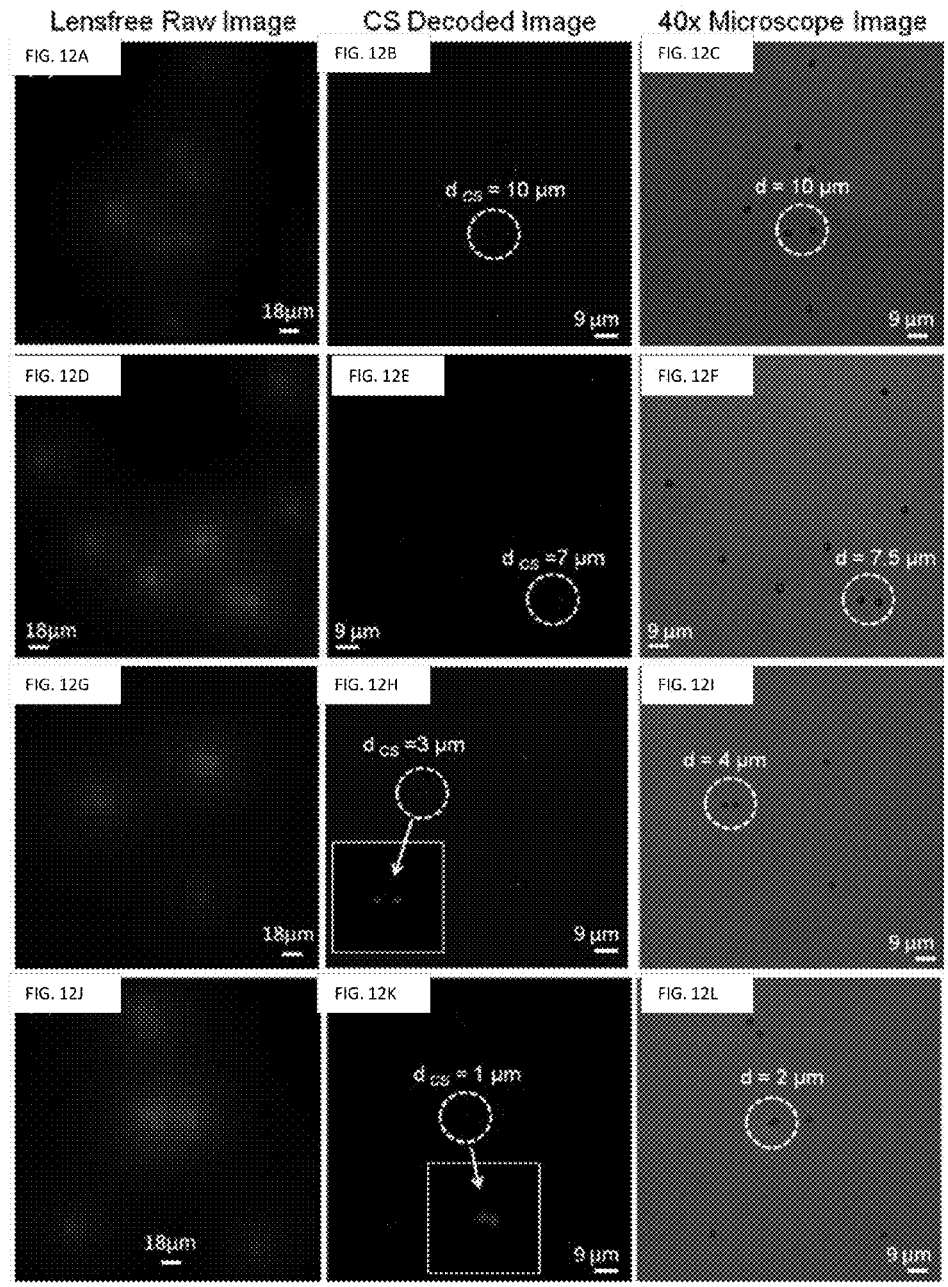

WIDE-FIELD LENSLESS FLUORESCENT IMAGING ON A CHIP

RELATED APPLICATION

This Application is a U.S. National Stage filing under 35 U.S.C. §371 of International Application No. PCT/US2011/033819, filed Apr. 25, 2011, which claims priority to U.S. Provisional Patent Application No. 61/330,799 filed on May 3, 2010 and U.S. Provisional Patent Application No. 61/430,449 filed on Jan. 6, 2011. The contents of the aforementioned applications are hereby incorporated herein by reference in their entirely. Priority to the aforementioned applications are hereby expressly claimed in accordance with 35 U.S.C. §§119, 120, 365 and 371 and any other applicable statutes.

FIELD OF THE INVENTION

The field of the invention generally relates to a device and method for on-chip fluorescent imaging over an ultra large field-of-view without the need for any lenses or mechanical scanning.

BACKGROUND OF THE INVENTION

For decades optical microscopy has been the workhorse of various fields including engineering, physical sciences, medicine and biology. Despite its long history, until relatively recently, there has not been a significant change in the design and working principles of optical microscopes. Over the last decade, motivated partially by the quest to better understand the realm of the nano-world, super-resolution techniques started a renaissance for optical microscopy by addressing some of the most fundamental limitations of optical imaging such as the diffraction limit. Besides these super-resolution techniques, several other novel imaging architectures were also implemented to improve the state of the art in optical microscopy towards better speed, signal to noise ratio (SNR), contrast, throughput, specificity, etc. This recent progress in microscopy utilized various innovative technologies to overcome the fundamental barriers in imaging and has created significant excitement in a diverse set of fields by enabling new discoveries to be made. However, together with this progress, the overall complexity and the cost of the optical imaging platform relatively increased which limits the wide spread use of some of these advanced optical imaging modalities beyond well equipped laboratories.

In the meantime, a rapid advancement in digital technologies has occurred, with much cheaper two-dimensional solid state detector arrays having significantly larger areas with smaller pixels, better dynamic ranges, frame rates and signal to noise ratios, as well as much faster, cheaper and more powerful digital processors and memories. This on-going digital revolution, when combined with advanced imaging theories and numerical algorithms, also creates an opportunity for optical imaging and microscopy to face another dimension in this renaissance towards simplification of the optical imaging apparatus, making it significantly more compact, cost-effective and easy to use, potentially without a trade-off in its performance. Lenses for decades have been helping detectors (analog or digital) to operate at the lowest possible space-bandwidth product that is determined by the desired field-of-view and the resolution of the image. However, the above discussed digital revolution has already advanced the state of the art for digital imagers such that a 2D space-bandwidth product of >10-20 Million is readily available nowadays. This implies that today's detector arrays are now much better suited to handle the information distortion caused by diffraction, which may then raise questions on the absolute necessity of the use of lenses in optical imaging. Moreover, today's digital processors together with novel algorithms are also in much better shape to process, almost instantaneously, the acquired information at the detector end for taking the job of a physical lens. With this in mind, one can conclude that the widespread use of lenses (or similar wavefront shaping elements) in optical imaging devices can now be potentially replaced for several application needs (specifically for cell microscopy) by cost-effective, compact and much simpler optical architectures that compensate in the digital domain for the lack of complexity of optical components. This approach should especially address the needs and the requirements of cytology, microfluidics, and resource-limited settings, potentially providing a leapfrog in the fight against various global health related problems involving infectious diseases.

SUMMARY

In one embodiment of the invention, an imaging device includes a sample holder configured to hold a sample, the sample holder having lower surface and a prism disposed adjacent the sample holder on a side opposite the lower surface of the sample holder. The device includes a light source configured to illuminate the sample via one face of the prism, wherein substantially all of the light is subject to total internal reflection at the lower surface of the sample holder. A fiber optic array is disposed adjacent to the lower surface of the sample holder, the fiber optic array having an input side and an output side. The device includes an imaging sensor array disposed adjacent to the output side of the fiber optic array.

In another embodiment of the invention, an imaging device includes a sample holder configured to hold a sample, the sample holder having lower surface. A hemispheric surface is disposed adjacent the sample holder on a side opposite the lower surface of the sample holder. The device includes a light source configured to illuminate the sample via the hemispheric surface, wherein substantially all of the light is subject to total internal reflection at the lower surface of the sample holder. A fiber optic array is disposed adjacent to the lower surface of the sample holder, the fiber optic array having an input side and an output side, wherein the input side of the fiber optic array has higher density of fiber optic waveguides compared to density of fiber optic waveguides at the output side. The device includes an imaging sensor array disposed adjacent to the output side of the fiber optic array.

In still another embodiment of the invention, a method of imaging a sample includes illuminating a sample contained in a sample holder with fluorescent excitation radiation passing through a prism prior illuminating the sample, wherein substantially all of the fluorescent excitation radiation is subject to total internal reflection at a lower surface of the sample holder and fluorescent emission radiation from the sample exits the sample holder. Image frames of the fluorescent emission radiation are acquired with the imaging sensor array. The acquired image frames are then subject to compressive decoding to produce decoded image frames.

BRIEF DESCRIPTION OF THE DRAWINGS

FIG. 4A illustrates a fluorescent image of 10 μm microparticles taken without the FOF.

FIG. 4B illustrates a fluorescent image of 10 μm microparticles taken with the FOF.

FIG. 4C1 illustrates a magnified view of region (c) in FIG. 4B obtained without the FOF.

FIG. 4C2 illustrates a magnified view of region (c) in FIG. 4B obtained with the FOF.

FIG. 4C3 illustrates a magnified view of region (c) that has been subject to compressive decoding.

FIG. 4D1 illustrates a magnified view of region (d) in FIG. 4B obtained without the FOF.

FIG. 4D2 illustrates a magnified view of region (d) in FIG. 4B obtained with the FOF.

FIG. 4D3 illustrates a magnified view of region (d) that has been subject to compressive decoding.

FIG. 4E1 illustrates a magnified view of region (e) in FIG. 4B obtained without the FOF.

FIG. 4E2 illustrates a magnified view of region (e) in FIG. 4B obtained with the FOF.

FIG. 4E3 illustrates a magnified view of region (e) that has been subject to compressive decoding.

FIG. 4F1 illustrates a magnified view of region (f) in FIG. 4B obtained without the FOF.

FIG. 4F2 illustrates a magnified view of region (f) in FIG. 4B obtained with the FOF.

FIG. 4F3 illustrates a magnified view of region (f) that has been subject to compressive decoding.

FIG. 5A illustrates a digitally-zoomed lensfree fluorescent image of a 10 μm particle obtained without any FOF.

FIG. 5B illustrates the output (decoded image frame) of a compressed decoded image of FIG. 5A.

FIG. 5C illustrates a digitally-zoomed lensfree fluorescent image of a 10 μm particle obtained with a FOF.

FIG. 5D illustrates the output (decoded image frame) of a compressed decoded image of FIG. 5C.

FIGS. 6A-6E illustrate lensfree fluorescent raw images taken of two fluorescent micro-objects (10 μm) at different separation distances obtained using an imaging device of FIG. 1A that were obtained with the use of a FOF.

FIGS. 6F-6J illustrate the resulting image frames after compressive decoding of the image frames of FIGS. 6A-6E.

FIGS. 6K-6O illustrate the deconvolution results of the Lucy-Richardson algorithm for the same set of lensfree images shown in FIGS. 6A-6E.

FIG. 7A illustrates a illustrate lensfree fluorescent raw images taken of two fluorescent micro-objects (2 μm) at a separation distance of 25 μm obtained using an imaging device of FIG. 1A.

FIG. 7B illustrates the resulting image frame after compressive decoding of the image frame of FIG. 7A.

FIG. 7C illustrates a illustrate lensfree fluorescent raw images taken of two fluorescent micro-objects (2 μm) at a separation distance of 19 μm obtained using an imaging device of FIG. 1A.

FIG. 7D illustrates the resulting image frame after compressive decoding of the image frame of FIG. 7C.

FIG. 7E illustrates a illustrate lensfree fluorescent raw images taken of two fluorescent micro-objects (2 μm) at a separation distance of 12 μm obtained using an imaging device of FIG. 1A.

FIG. 7F illustrates the resulting image frame after compressive decoding of the image frame of FIG. 7E.

FIG. 7G illustrates a illustrate lensfree fluorescent raw images taken of two fluorescent micro-objects (2 μm) at a separation distance of 7 μm obtained using an imaging device of FIG. 1A.

FIG. 7H illustrates the resulting image frame after compressive decoding of the image frame of FIG. 7G.

FIG. 8A illustrates a illustrate lensfree fluorescent raw images taken of two fluorescent micro-objects (2 μm) at a separation distance of 25 μm obtained using an imaging device of FIG. 1A.

FIG. 8B illustrates the resulting image frame after compressive decoding of the image frame of FIG. 8A.

FIG. 8C illustrates a illustrate lensfree fluorescent raw images taken of two fluorescent micro-objects (2 μm) at a separation distance of 19 μm obtained using an imaging device of FIG. 1A.

FIG. 8D illustrates the resulting image frame after compressive decoding of the image frame of FIG. 8C.

FIG. 8E illustrates a illustrate lensfree fluorescent raw images taken of two fluorescent micro-objects (2 μm) at a separation distance of 12 μm obtained using an imaging device of FIG. 1A.

FIG. 8F illustrates the resulting image frame after compressive decoding of the image frame of FIG. 8E.

FIG. 8G illustrates a illustrate lensfree fluorescent raw images taken of two fluorescent micro-objects (2 μm) at a separation distance of 8 μm obtained using an imaging device of FIG. 1A.

FIG. 8H illustrates the resulting image frame after compressive decoding of the image frame of FIG. 8G.

FIG. 9A illustrates the two layers (Layer 1 and Layer 2) that were imaged with a $\Delta z$ of 50 μm between layers using an imaging device.

FIG. 9B illustrate lensfree raw images obtained from a digitally-cropped region of the large FOV that were imaged without the use of the FOF.

FIG. 9C illustrate the compressive decoding results for the Layer 1 of the raw image of FIG. 9B.

FIG. 9D illustrate the compressive decoding results for the Layer 2 of the raw image of FIG. 9B.

FIG. 9E illustrates lensfree raw images obtained from a digitally-cropped region of the large FOV that were imaged with the FOF.

FIG. 9F illustrate the compressive decoding results for the Layer 1 of the raw image of FIG. 9E.

FIG. 9G illustrate the compressive decoding results for the Layer 2 of the raw image of FIG. 9E.

FIG. 9H illustrates a lensfree raw image obtained from a different digitally-cropped region of the large FOV that was imaged without the use of the FOF.

FIG. 9I illustrate the compressive decoding results for the Layer 1 of the raw image of FIG. 9H.

FIG. 9J illustrate the compressive decoding results for the Layer 2 of the raw image of FIG. 9H.

FIG. 9K illustrates a lensfree raw image obtained from a different digitally-cropped region of the large FOV that were imaged with the FOF.

FIG. 9L illustrate the compressive decoding results for the Layer 1 of the raw image of FIG. 9K.

FIG. 9M illustrate the compressive decoding results for the Layer 2 of the raw image of FIG. 9K.

FIG. 11A illustrates the entire imaging FOV (~60 mm²) of an imaging device of FIG. 10A.

FIG. 11B illustrates the raw image frame of a portion of the lensfree fluorescent image.

FIG. 11C illustrates the decoded image frame after compressive decoding.

FIG. 11D illustrates microscopic images of the same micro-particles (4 μm diameter) using a conventional lens-based fluorescent microscope (10× objective lens, NA=0.25).

FIG. 12A illustrates a raw image of 2 μm diameter particles imaged with the imaging device of FIG. 10A.

FIG. 12B illustrates the decoded image frame of FIG. 12A.

FIG. 12C illustrates a microscope image of the FOV of FIG. 12A.

FIG. 12D illustrates a raw image of 2 μm diameter particles imaged with the imaging device of FIG. 10A.

FIG. 12E illustrates the decoded image frame of FIG. 12D.

FIG. 12F illustrates a microscope image of the FOV of FIG. 12D.

FIG. 12G illustrates a raw image of 2 μm diameter particles imaged with the imaging device of FIG. 10A.

FIG. 12H illustrates the decoded image frame of FIG. 12G.

FIG. 12I illustrates a microscope image of the FOV of FIG. 12G.

FIG. 12J illustrates a raw image of 2 μm diameter particles imaged with the imaging device of FIG. 10A.

FIG. 12K illustrates the decoded image frame of FIG. 12J.

FIG. 12L illustrates a microscope image of the FOV of FIG. 12J.

DETAILED DESCRIPTION OF THE ILLUSTRATED EMBODIMENTS

Figure 1A:
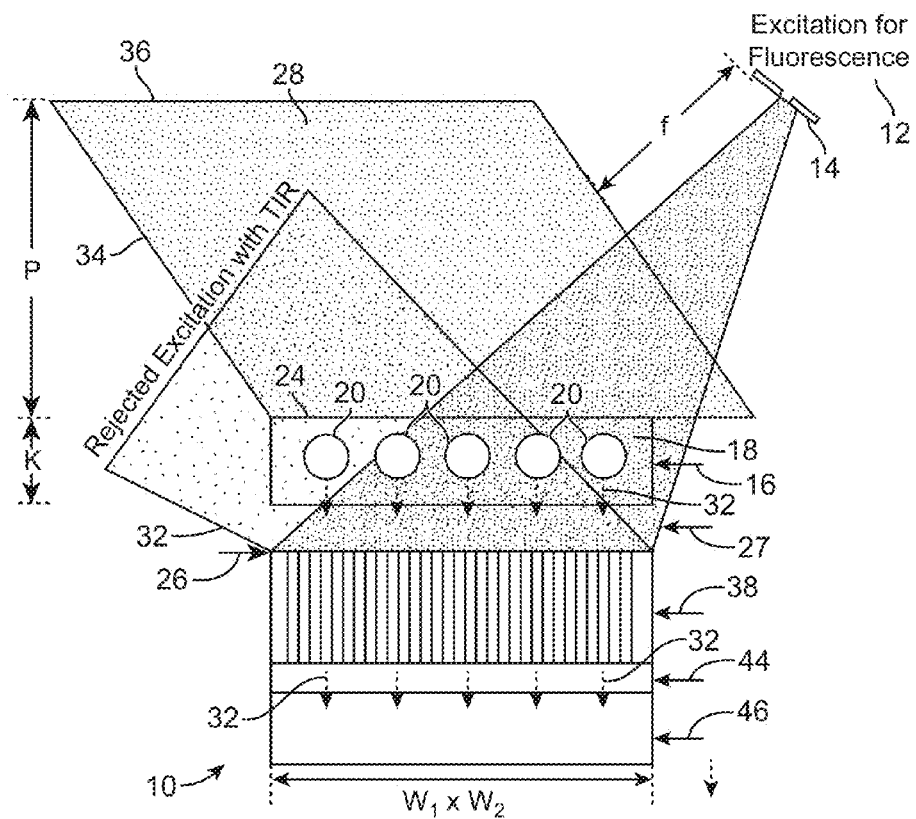
FIG. 1A is a schematic representation of an imaging device according to one embodiment. The fiber optic faceplate (FOE) is interposed between the sample holder and the imaging sensor array.

FIG. 1A illustrates an imaging device 10 according to one embodiment of the invention. The imaging device 10 includes a light source 12 that serves as an excitation light source of fluorescence as explained in more detail below. The light source 12 may include any number light sources capable of acting as a fluorescent pump. These include, by way of example, diodes, lasers, LEDs, or even a filtered light source such as, for instance, a Xenon lamp coupled to a monochromatic filter. As seen in FIG. 1A, the light source 12 may include an optional aperture 14, through which, the light passes. Alternatively, the light source 12 may include a fiber optic cable (e.g., multi-mode fiber optic cable).

Figure 2:
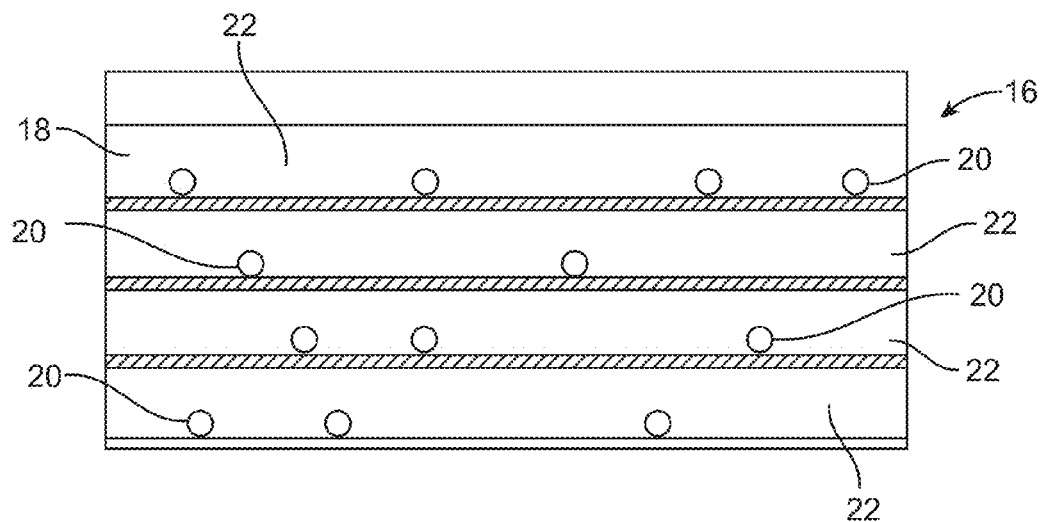
FIG. 2 is a side view of a sample holder having a plurality of micro-channels located at different vertical locations.

Still referring to FIG. 1A, the imaging device 10 includes a sample holder 16 that is configured to hold a sample 18. The sample 18 may include micro-objects 20 that may be biological or non-biological in origin. As one example, the micro-objects 20 of the sample 18 may include, for example, cells, organelles, or the like that is labeled with one or more fluorescent moieties. The sample holder 16 may include a three-dimensional volume or space in which a sample 18 is placed. Alternatively, the sample holder 16 may include one or more micro-channels 22 such as that illustrated in FIG. 2. FIG. 2 illustrates four (4) vertically stacked micro-channels 22. The micro-channels 22 may be used for flow-based imaging applications. For example, a sample 18 which may comprise a fluid that contains a population of cells or the like may be pumped or otherwise flowed through the micro-channels 22. The micro-channels 22, when stacked, allow for parallel imaging and decoding. This may be particularly suited when there is a need for the rapid imaging and/or screening of rare events (e.g., cancer screening a larger population of cells) or even in DNA or protein micro-array applications.

As seen in FIG. 1A, the sample holder 16 includes an upper surface 24 and a lower surface 26. In the embodiment illustrated in FIG. 1A, the lower surface 26 of the sample holder 16 is the lower surface of a coverglass having a thickness of 50 μm. As seen in FIG. 1A, a prism 28 is disposed atop the sample holder 16. The prism 28 has multiple faces. The pumped light source 12 enters one of the faces 30 of the prism 28 and passes through the sample holder 16. The pumped light source 12 interacts with the micro-objects 20, causing the emission of fluorescent light as represented by arrows 32 in FIG. 1A. The pumped light from light source 12, in the form of propagating waves, faces total internal reflection (TIR) after exciting the entire sample 18. In the embodiment of FIG. 1A, TIR occurs at the lower surface 26 and, in particular, the glass-air interface at the bottom facet of the coverglass. The pumped light subject to TIR is reflected and rejected via faces 34, 36 of prism 28.

Figure 1B:
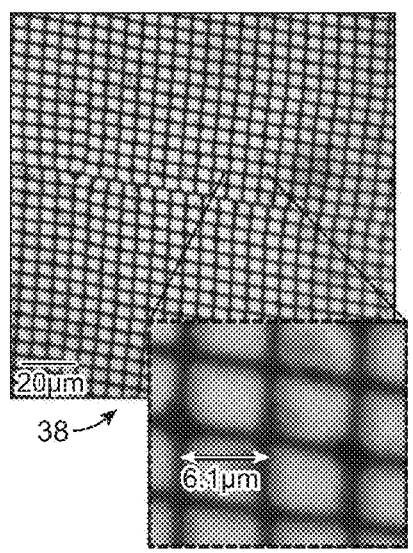
FIG. 1B is a microscope image of the FOF of FIG. 1A. The numerical aperture of each fiber within the FOF is approximately 0.3.

Still referring to FIG. 1A, the fluorescent emission 32 from the excited micro-objects 20 is then collected using a dense a fiber optic faceplate (FOF) 38. The FOF 38 is an array of fiber optic waveguides having an input side 40 and an output side 42. In the embodiment illustrated in FIGS. 1A and 1B, the numerical aperture of each fiber within the FOF 38 is approximately 0.3. The period of each fiber within the FOF 38 was approximately 6 μm. The thickness of the FOF 38 illustrated in FIG. 1A is around 1 cm. Generally, a thickness of the FOF 38 within the range of about 100 μm to about 5 cm will be sufficient. A microscopic end-view image of the FOF 38 is illustrated in FIG. 1B along with a magnified portion. In this embodiment, the FOF 38 does have any physical magnification and therefore has a field-of-view (FOV) that is equivalent to the detector active area which is described in more detail below.

The fluorescent emission 32, after exiting the output side 42 of the FOF 38 passes through an absorption filter 44. The absorption filter 44 is used to eliminate or mitigate the detection of scattered photos from the pimped light source 12. The absorption filter 44 illustrated in FIG. 1A is a plastic-based absorption filter having a thickness between 75 μm and 100 μm. The absorption filter 44 permits passage of the fluorescent emission 32. As seen in FIG. 1A, this fluorescent emission 32 passes to an imaging sensor array 46. The imaging sensor array 46 preferably has a relatively large detector active area, for example, larger than 8 cm² although other sizes will also work (e.g., within a range of about 1 mm² to about 20 cm²). The imaging sensor array 46 may include a CMOS or CCD device that is commercially available. FIG. 1A illustrates a large format CCD available from KODAK (CAI-11002) with a pixel size of 9 μm and an active area of 25 mm×25 mm.

With reference to FIG. 1A, typical dimensions of the device 10 include $w_1 \times w_2 = 25$ mm×35 mm; p=1.7 cm; k~10-100 μm; f=1-2 cm. Of course, these dimensions may change or vary beyond those specifically set forth above.

Figure 3A:
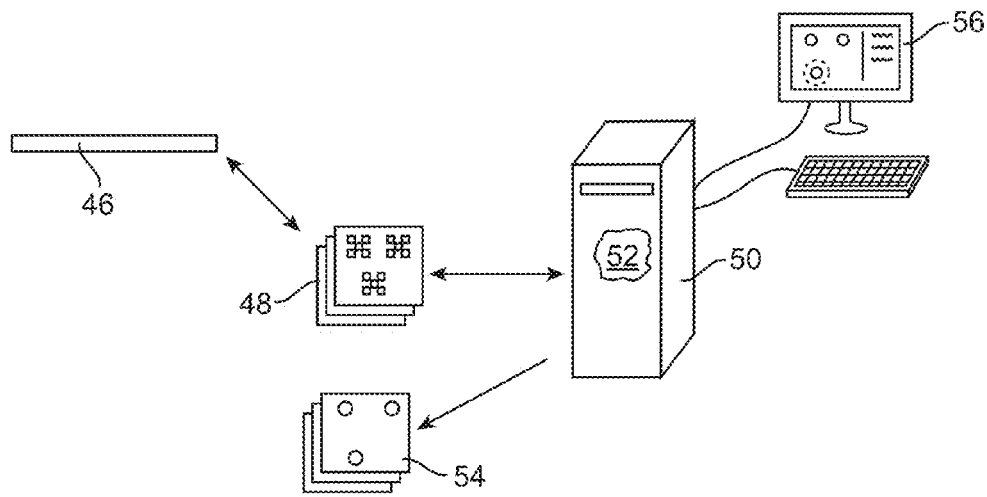
FIG. 3A schematically represents the acquisition and compressive decoding operation used in the method of imaging a sample according to one embodiment of the invention.

The imaging sensor array 46 is used to acquire raw image frames 48. As seen in FIG. 3A, these raw image frames 48 are transferred or otherwise communicated to a computer 50 or other microprocessor(s) for subsequent data processing. In particular, the computer 50 is loaded with or otherwise adapted to contain a compressive decoding algorithm 52. As explained in more detail below, the compressive decoding algorithm 52 is applied to the raw image frames 48 to produce decoded image frames 54. The compressive decoding algorithm 52 recovers the distribution of fluorescent points that created the two-dimensional (2D) lensless image that was sampled at the imaging sensor array 46. The decoded image frames 54 may be displayed, for example, on a display 56 associated with the computer 50. The decoded image frames 54 may also be subject to additional image processing steps. For example, the decoded image frames 54 may be analyzed for certain rare micro-objects 20 that may be imaged such as a cell that displays a particular rare phenotype (e.g., cancer). The computer 50 may identify such a cell and highlight the same to the user.

Figure 3B:
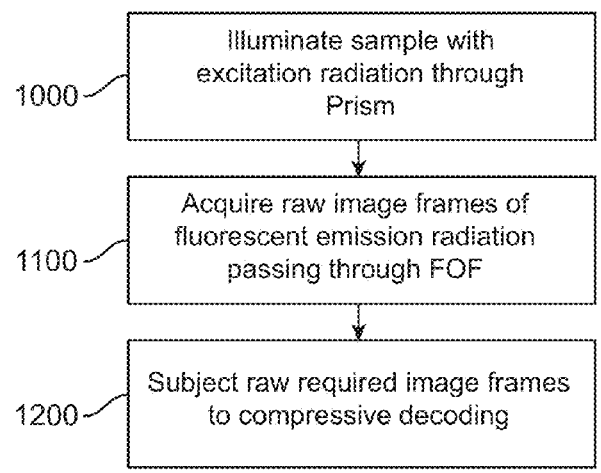
FIG. 3B represents operations for imaging a sample according to one embodiment of the invention.

FIG. 3B illustrates the order of operations used to image a sample using the device 10 illustrated in FIG. 1A. In operation 1000, a light source 12 is used to illuminate the sample 18 with excitation radiation through a prism 28. In operation 1100, raw image frames 48 of fluorescent radiation passing through the FOF 38 are obtained at the imaging sensor array 46. In operation 1200, the raw image frames 48 are then subject to a compressive decoding algorithm 52 to generate decoded image frames 54.

To briefly go over the relationship between lensfree fluorescent imaging on a chip and compressive sampling theory, one can denote the fluorescent particle/cell distribution within the sample volume with $\bar{c}=[c_1, c_2, \ldots, c_N]$ where N denotes the number of voxels. To better relate this model to a real imaging experiment, let one also assume that the physical grid size in $\bar{c}$ is d. For visualization purposes, one can think of a simple microfluidic channel such that $\bar{c}$ would represent the points on the active surface of the channel, where the captured cells reside within an imaging area of $N \times d^2$. For multi-layered micro-channels, however, $\bar{c}$ would represent a 3D discreet volume.

For the applications that are of interest to this work, such as wide-field fluorescent cytometry, rare cell analysis and high-throughput micro-array imaging, one can, in general, assume that $\bar{c}$ is sparse to start with, such that only S coefficients of $\bar{c}$ are non-zero, where S<<N. This assumption is further justified with our unit magnification lensless geometry since most cells of interest would not be over-sampled due to limited spatial resolution, restricting the value of S for a practical $\bar{c}$. Therefore, the sparsity of $\bar{c}$ is the first connection to compressive sampling, as it is an important requirement of its underlying theory.

In a lensfree fluorescent imaging platform as shown in FIG. 1A, $\bar{c}$ uniquely determines the intensity distribution that is impinging on the imaging sensor array 46. For each non-zero element of $\bar{c}$, a wave is transmitted, and after passing through different layers on the sample holder 16 it incoherently adds up with the waves created by the other fluorescent points within the sample volume. Therefore, one can write the intensity distribution right above the detector plane (before being measured/sampled) as:

$$f(x, y) = \sum_{i=1}^{N} c_i \psi_i(x, y) \quad (1)$$

where $\psi_i(x,y)$ represents the 2D wave intensity right before the detector plane that originated from the physical location of $c_i$. The analytical form of $\psi_i$ can be derived for any particular lensfree geometry such as the one presented in FIG. 1A. However, from a practical point of view, it can easily be measured for each object plane by using e.g., small fluorescent micro-objects 20.

Without the use of a faceplate in FIG. 1A, it is straightforward to see that the functional form of $\psi_i$, for a given object plane is space invariant. This is equivalent to say that $\psi_i(x,y) = p(x-x_i, y-y_i)$, where $p(x,y)$ is the incoherent point-spread function (psf) of the system for a given object layer, and $(x_i, y_i)$ denotes the physical location of $c_i$. Note that in this definition, $p(x,y)$ has no relationship to the pixel size at the detector since Eq. (1) describes the intensity right before the sampling plane. The same space invariance property also holds with a dense FOF 38 as shown in FIG. 1A since there is a significant gap between the sample and faceplate planes, and a similar gap between the bottom surface of the faceplate and the detector plane. Therefore for the lensfree fluorescent imaging geometry of FIG. 1A, with or without the faceplate operation, one can in general write:

$$f(x, y) = \sum_{i=1}^{N} c_i p(x - x_i, y - y_i) \quad (2)$$

For multiple layers of fluorescent micro-objects 20, a similar equation could also be written where the incoherent point-spread function of different layers are also included in the summation.

Equation (2) relates the "already" sparse fluorescent object distribution ($\bar{c}$) to an optical intensity distribution that is yet to be sampled by the imaging sensor array 46. The representation basis provided by $\psi_i(x,y)$ is not an orthogonal one since it is based on lensfree diffraction. This is not limiting the applicability of compressive decoding to this work since $\bar{c}$ is assumed to be already sparse, independent of the representation basis. On the other hand, the fact that $\psi_i(x,y)$ does not form an orthogonal basis limits the spatial resolution that can be compressively decoded, since for closely spaced $c_i$ values, the corresponding $\psi_i(x,y)$ would be quite similar to each other for a given detection signal to noise ratio (SNR). This is related to the restricted isometry property of the system as will be discussed later on; however its physical implication is nothing new since it is already known that we trade off spatial resolution to achieve wide-field lensfree fluorescent imaging with unit magnification.

Next, sampling of f(x,y) at the detector-array can be formulated as:

$$I_m = \iint f(x,y) \cdot \phi(x-x_m, y-y_m) \cdot dx \cdot dy \quad (3)$$

where $\Phi_m = \phi(x-x_m, y-y_m)$ represents the sampling/measurement basis; m=1:M denotes the $m^{th}$ pixel of the detector-array with center coordinates of $(x_m, y_m)$; and $\phi(x,y)$ represents the pixel function, which can be approximated to be a detection constant, K, for $|x|,|y| \leq W/2$ (assuming a square pixel size of W) and 0 elsewhere, $|x|,|y| > W/2$. In this notation, the fill-factor of the imaging sensor array 46 together with the quantum efficiency, etc. are all lumped into K. Note that in this example, we have used W=9 μm and W=18 μm (through pixel binning).

With these definitions, the lensfree fluorescent imaging problem can be summarized as such: based on M independent measurements of $I_m$, we would like to estimate the sparse fluorescent source distribution, $\bar{c}$ at the sample.

To give more insight, Eq. (3) models a hypothetical near-field sampling experiment, where each pixel of the imaging sensor array 46 measures part of f(x,y). For an arbitrary intensity distribution f(x,y) impinging on the imaging sensor array 46, a few pixel values ($I_m$) can surely not represent the entire function. However, if the sampled intensity profile at the detector plane is created by a sparse distribution of incoherent point sources located in the far-field, then much fewer pixels can potentially be used to recover the source distribution based on compressive decoding. For this decoding to work efficiently, each pixel should ideally detect "some" contribution from all the $c_i$ values, which implies the need for a relatively wide point spread function (psf). However since spreading of the fluorescence also decreases the signal strength at the detector plane, the optimum extent of the point spread function is practically determined by the detection SNR. On one extreme, if the same sparse source distribution ($\bar{c}$) was hypothetically placed in direct contact with the imaging sensor array 46 pixels, this would not permit any compressive decoding since each incoherent point source can now only contribute to a single pixel value. For instance two sub-pixel point sources that are located on the same pixel would only contribute to that particular pixel, which would make their separation physically impossible regardless of the measurement SNR. However, the same two sub-pixel point sources could be separated from each other through compressive decoding if they were placed some distance above the detector plane, such that more pixels could detect weighted contributions of their emission.

Because we are considering non-adaptive imaging here (i.e., no a priori information about the possible x-y locations of the fluorescent particles/cells), we have not used a sub-set of the pixel values ($I_m$) to reconstruct $\bar{c}$. Therefore, for a single layer of object, using a unit magnification as in FIG. 1A, we have $N \times d^2 = M \times W^2$. Here, to claim a spatial resolution of ~10 μm at the object plane, we used d=2-3 μm, which implies N≥9M for W=9 μm. For some experiments, a pixel size of W=18 μm with d=2 μm has also been used, implying N=81M. Furthermore, for multi-layer experiments where three (3) different fluorescent micro-channels 22 were vertically stacked and simultaneously imaged in a single snap-shot, N=27M, which all indicate compressive imaging since the number of measurements (M) are significantly smaller than the number of reconstructed points (N).

The effectiveness of the decoding process to estimate $\bar{c}$ in this technique should also depend on the maximum spatial correlation between $\Phi_m$ and $\psi_i$ for all possible m=1:M and i=1:N pairs. Accordingly, this maximum spatial correlation coefficient defines the measure of incoherence between sampling and representation bases, which can then be related to the probability of accurately reconstructing $\bar{c}$ from M measurements. For a given object plane, because of the shift invariant nature of both $\Phi_m$ and $\psi_i$, this coherence calculation is equivalent to calculation of the correlation between the pixel function $\phi(x,y)$ and the incoherent point-spread function $p(x,y)$. The smaller the correlation between these two spatial functions is, the more accurate and efficient the compressive decoding process gets. Based on this, a smaller pixel size would further help in the lensfree on-chip scheme by reducing this maximum correlation coefficient, i.e., increasing incoherence between $\Phi_m$ and $\psi_i$.

Thus, we can conclude that the primary function of compressive sampling described herein is to digitally undo the effect of diffraction induced spreading formulated in Eqs. 1-2 through decoding of lensfree image pixels indicated in Eq. 3. Such a decoding process, however, can also be done physically rather than digitally, through the use of a lens (as in conventional fluorescent microscopy at the cost of reduced FOV) or through the use of a FOF 38. The use of the FOF 38 in FIG. 1A partially decodes the diffraction induced spreading, which also relatively increases the correlation between $\phi(x,y)$ and $p(x,y)$, since $p(x,y)$ gets narrower and stronger with the FOF 38. Despite this relatively increased coherence between the sampling and representation bases, the improvement in the detection SNR with the FOF 38 enables better measurement of $p(x,y)$ as well as $I_m$, values, which then improves the accuracy of the compressive decoding process in terms of achievable spatial resolution.

It is noteworthy that the above analysis could be also done using a different set of measurement and representation bases without changing the end conclusions. In the above analysis, the diffraction process was not included as part of the measurement, and therefore the measurement basis only involved the pixel sampling at the imaging sensor array 46. As an alternative notation, one could have also used $\psi_i(x,y)=\delta(x-x_i, y-y_i)$ for the representation basis, which implies that $\Psi$ is an identity matrix. This is not a surprising choice since the object, $\bar{c}$ is already sparse and therefore the sparsifying matrix can be seen as an identity matrix. Based on this definition of the representation basis, the measurement basis $\Phi_m$ will now need to include both the diffraction and the pixel sampling processes. Following a similar derivation as in Eq. 3, the measurement basis now becomes:

$$\Phi_m = \iint p(x-x_i, y-y_i) \cdot \phi(x-x_m, y-y_m) \cdot dx \cdot dy \quad (4)$$

As expected, the correlation behavior between $\Phi_m$ and $\psi_i$, for all possible m and i pairs remains the same as before, yielding the same set of conclusions that we arrived using the previously discussed choice of bases.

While it is just a matter of notation, with this new pair of bases, it is also easier to qualitatively relate the spatial resolution to restricted isometry property (RIP) of the system. RIP is a measure of the robustness of sparse signal reconstruction for N>M and S<<N. For this new choice of bases, RIP holds if all the possible subsets of S columns taken from $\Phi\Psi=\Phi$ are nearly orthogonal to each other. Assuming that the pixel size is much narrower than the incoherent psf of the object layer of interest, we can then approximate:

$$\Phi_m \approx p(x_m-x_i, y_m-y_i) \cdot \iint \phi(x-x_m, y-y_m) \cdot dx \cdot dy = K \cdot W^2 p(x_m-x_i, y_m-y_i) \quad (5)$$

Therefore for RIP to hold in this lensfree system, for any arbitrary S choices of i=1:N, the sub-set of functions $\Phi_m \approx K \cdot W^2 \cdot p(x_m-x_i, y_m-y_i)$ should be nearly orthogonal in $(x_m, y_m)$. If one purely relies on diffraction, this condition can be harder to satisfy for densely spaced $(x_i, y_i)$ which practically limits the achievable spatial resolution for a given detection SNR. Once again, physically this is not surprising since it is already known that we trade off resolution to achieve wide-field lensfree fluorescent imaging on a chip. Structured surfaces could potentially help achieving a better resolution by randomly breaking the space invariance of the incoherent psf.

As discussed in above, the main function of the compressive sampling theory is to recover the distribution of the fluorescent points that created the 2D lensless image sampled at the detector array. Knowing the incoherent psf of our system for each object layer, for an arbitrary distribution of fluorescent sources (within e.g., a single micro-channel 22 or a stack of vertical micro-channels 22), one can easily calculate the expected lensfree image at the detector-array. Using this fact, through a compressive sampling algorithm the distribution of the fluorescent sources at the object volume based on a given 2D lensless fluorescent measurement can be optimized. The particular compressive sampling algorithm used was based on the algorithm set forth in S.-J. Kim et al., "An Interior-Point Method for Large-Scale l1-Regularized Least Squares", IEEE Journal on Selected Topics in Signal Processing, 1(4): 606-617, (December, 2007), which is incorporated by reference herein. The choice of this particular compressive decoder is highly suitable for the presented wide FOV fluorescent imaging platform since it is especially designed for sparse signal recovery from large data sets.

To be more specific, the reconstruction/decoding process can be formulized as an $l_1$-regularized least squares problem (LSP), such that:

$$\hat{c} = \mathrm{argmin} \|I_{det} - M_{conv} \cdot \bar{c}\|_2 + \beta \cdot \|\bar{c}\|_1 \quad (6)$$

where $\beta > 0$ is a regularization parameter; $I_{det}$ is the detected raw fluorescent image at the sensor-array (in a vector form); $M_{conv}$ represents the 2D convolution matrix based on the incoherent point spread function of the system; $\bar{c}$ is the fluorescent source distribution that creates the lensfree image at the detector plane; and $$\|\bar{x}\|_p = \left( \sum_{i=1}^{n} |x_i|^p \right)^{1/p}$$

represents the $I_p$ norm of vector $\bar{x}$. For multiple micro-channels 22 that are vertically stacked, there is a separate $M_{conv}$ for each source layer. The compressive decoding algorithm 52 used here is based on truncated Newton interior-point method and rapidly provides a sparse solution ($\hat{c}$) for Eq. (6) especially for large-scale data sets using a non-negativity constraint, which is surely satisfied for fluorescent imaging in general.

Experimental Results

First Embodiment

To validate and quantify the performance of the imaging device 10 and method of imaging, fluorescent micro-particles (2 μm and 10 μm diameter) were imaged using the lensfree set-up of FIG. 1A. The light source 12 had an excitation wavelength of 495 nm and fluorescent radiation was emitted at 505 nm. In this set-up, a large format CCD was used for the imaging sensor array 46 (KAI-11002 available from KODAK, pixel size: 9 μm, active area: 25 mm×35 mm) together with a fiber-optic faceplate where the numerical aperture of each fiber was ~0.3 with a period of ~6 μm. FIG. 1B illustrates the end view of the FOF 38 that was used. The results of these fluorescent imaging experiments are summarized and described below which point to several important features of our platform.

As seen in FIGS. 4A and 4B, the presence of the FOF 38 in the imaging device 10 significantly reduces the diffraction induced spreading of the fluorescent signatures of the objects. Specifically, as seen in FIG. 4A, the FWHM of the fluorescent signatures at the detector plane is now reduced by ~5 fold, from ~180 μm down to ~36 μm using the FOF 38. Note that except the faceplate thickness, all the other vertical distances are kept the same in both configurations—with and without the faceplate—to provide a controlled comparison). This improvement is quite significant as it permits a better detection SNR and a higher spatial resolution to be achieved The physical function of the FOF 38 used in the experiments is to collect the fluorescent emission from the specimen with an effective numerical aperture of ~0.3 and to guide it to the imaging sensor array 46. However, since the fluorescent emission from the micro-objects 20 spreads with an effective numerical aperture of 1 over the air gap above the FOF 38, several oblique fluorescent rays (corresponding to higher angles than the acceptance NA of each fiber) remain unguided. These unguided rays (which undergo various partial reflections over multiple fiber cross-sections) are also detected at the sensor plane and are incoherently superimposed onto the fluorescent signal that is guided through the core of each fiber. However, since the thickness of the FOF 38 is relatively large (~1 cm), the contribution of these unguided fluorescent waves is weaker than the guided fluorescent signal.

Therefore, the FOF 38 used in the imaging device 10, even though significantly reduces the signal spreading at the detector plane as shown in FIG. 4, also brings its own distortion to the recorded images by creating a unique incoherent point-spread function (psf) at the detector plane. The exact spatial form of this 2D incoherent point-spread function is determined by the faceplate periodicity and lattice, numerical aperture of the individual fibers, the distance between the sample plane and the upper surface of the FOF 38, as well as the distance between the exit plane of the FOF 38 and the detector array. Once all these parameters are fixed in the imaging geometry as illustrated in the configuration of FIG. 1A, the resulting psf for a given object plane is easily measured using e.g., small diameter fluorescent particles that are imaged at a low concentration. Moreover, the physical gap (~1-500 μm) between the sample and the faceplate planes, together with the gap between the faceplate and the detector planes (~1-500 μm) ensure that this incoherent point spread function is space invariant all across our imaging FOV, which enables the use of a single point spread function for decoding of each object plane.

FIGS. 5A-5D illustrate images comparing the performance of the imaging device 10 with and without the FOF 38 for decoding the same field-of-view. As seen in FIGS. 5C and 5D there clearly is superior performance in the FOF decoded images in terms of resolving closely spaced fluorescent particles without any reconstruction artifacts or ambiguities. This can be seen by the arrows in FIGS. 5B, 5C, and 5D.

FIGS. 6A-6E illustrate lensfree fluorescent raw images taken of two fluorescent micro-objects 20 (10 μm) at different separation distances obtained using an imaging device 10 of FIG. 1A that were obtained with the use of a FOF 38. The inset images in the FIGS. 6A-6E (bottom right corner of each image) illustrate transmission microscope images of the same particles from which the center-to-center distance (g) in each case is calculated only for comparison purposes. FIGS. 6F-6J illustrate the resulting image frames after compressive decoding of the image frames of FIGS. 6A-6E. In FIGS. 6A-6E $g_{CS}$ refers to the center-to-center distance of the resolved fluorescent particles in each image, where CS denotes "compressive sampling." Even for g=10 μm case (far right column), one can clearly resolve the fluorescent micro-objects 20 from each other with $g_{CS}$=9 μm. The pixel size in the decoded image is 3 μm, whereas the raw lensfree image has been sampled with a pixel size of W=9 μm at the detector array, i.e., N=9M. The reason that the reconstructed points for $g_{CS}$=9 μm case do not touch each other (unlike the microscope image shown in the inset) is that the incoherent point-spread function of the system has been estimated using 10 μm diameter fluorescent particles.

The computation times of these decoded images vary between 0.1 min to 0.5 min on an Intel Centrino Duo Core, 1 GHz PC. FIGS. 6K-6O illustrate the de-convolution results of the Lucy-Richardson algorithm for the same set of lensfree images shown in FIGS. 6A-6E. In FIGS. 6K-6O, $g_{LR}$ refers to the center-to-center distance of the resolved fluorescent particles in each image, where LR denotes "Lucy-Richardson."

The number of iterations in these de-convolution results ranged between 200 and 400, matching with the overall computation time of the CS results for each image. These results indicate that the LR algorithm can resolve particles with g~18 µm, whereas the CS decoder can clearly resolve particles with g~10 µm.

FIGS. 7A-7H illustrate lensfree fluorescent raw images as well as their compressively decoded images taken of two fluorescent micro-objects 20 (2 µm in diameter) at different separation distances. Images were obtained using an imaging device 10 of FIG. 1A that were obtained with the use of a FOF 38. The raw lensfree images (FIGS. 7A, 7C, 7E, 7G) are decoded to resolve closely spaced particles from each other. The inset images (bottom right corner of each decoded image in FIGS. 7B, 7D, 7F, 7H) illustrate regular transmission microscope images of the same particles from which the center-to-center distance (g) in each case is calculated for comparison purposes. The bottom row illustrates resolving 2 µm micro-objects 20 that are separated by g~12 µm and 8 µm respectively. The pixel size in the raw lensfree fluorescent images is W=9 µm, whereas the pixel size of the decoded images is 2 µm, i.e., N~20M. The point-spread function of the system has been estimated using 2 µm diameter fluorescent particles imaged at a low concentration.

FIGS. 8A-8H illustrate lensfree fluorescent raw images as well as their compressively decoded images taken of two fluorescent micro-objects 20 (2 µm in diameter) at different separation distances. Images were obtained using an imaging device 10 of FIG. 1A that were obtained with the use of a FOF 38. Unlike FIGS. 7A-7H, the pixel size of W=18 µm at the imaging sensor array 46 such that four (4) pixels of the imaging sensor array 46 are decoded to resolve closely spaced fluorescent micro-objects 20 from each other. The pixel size of the decoded images is still 2 µm, same as in FIGS. 7A-7H, which this time implies N=81M. Because of a significant reduction in M when compared to FIGS. 7A-7H, the performance of the compressive decoding is relatively degraded, which is especially visible for reconstruction of g=8 µm case (bottom right corner). Regardless, even with N=81M, the device and method have achieved decoding of sub-pixel objects as shown in FIG. 8F (e.g., g=12 µm).

Another aspect of the imaging device 10 and method is the ability to reconstruct the distribution of fluorescent micro-objects 20 located at multiple micro-channels 22 that are stacked vertically. This enables the imaging device 10 and method to decode the two-dimensional (2D) lensfree fluorescent image at the imaging sensor array 46 into a three-dimensional (3D) distribution through compressive sampling, which is especially important to further increase the throughput of fluorescent on-chip imaging applications.

FIGS. 9A-9M illustrate images where the fluorescent micro-particles 20 (10 µm in diameter) located at two different micro-channels 22 were imaged and decoded all in parallel. While two different micro-channels 22 were used in this particular experiment, the same imaging and decoding techniques can be used to decode additional layered micro-channels 22 such as those illustrate in FIG. 2. In these experiments the fluorescent channels were vertically separated by 50 µm. FIG. 9A illustrates the two layers (Layer 1 and Layer 2) that were imaged with a Δz of 50 µm between layers. FIGS. 9B and 9H illustrate lensfree raw images obtained from two different digitally-cropped regions of the large FOV that were imaged without the use of the FOF 38. FIGS. 9C and 9D illustrate the compressive decoding results for the two layers of the raw image of FIG. 9B. FIGS. 9I and 9J illustrate the compressive decoding results for the two layers of the raw image of FIG. 9H. FIGS. 9E and 9K illustrate lensfree raw images obtained from two different digitally-cropped regions of the large FOV that were imaged with the FOF 38. FIGS. 9F and 9G illustrate the compressive decoding results for the two layers of the raw image of FIG. 9E. FIGS. 9L and 9M illustrate the compressive decoding results for the two layers of the raw image of FIG. 9K. As seen in FIGS. 9B-9M, the superior performance of the FOF 38 for resolving overlapping fluorescent signatures from each other is evident.

A quantitative comparison of the presented compressive sampling based reconstruction approach can be made with some of the existing deconvolution methods that could potentially be used for the same purpose. One such numerical recipe is the Lucy-Richardson algorithm which relies on the knowledge of the incoherent point spread function (psf) to iteratively converge to the maximum-likelihood estimation of the fluorescence source distribution based on the detected image. This algorithm is not restricted to sparse objects only and has been shown to be quite effective converging within typically a few hundred iterations to the source distribution. A comparison of the performance of this algorithm against compressive sampling based reconstruction is illustrated in FIGS. 6K-6O, which clearly indicates the advantages of the compressive decoding approach especially in terms of spatial resolution. A comparison of FIGS. 6F-6J with FIGS. 6K-6O demonstrates that, for the same set of lensless fluorescent measurements, the compressive decoder achieves ~10 µm resolution, while the Lucy-Richardson deconvolution algorithm achieves ~20 µm. This behavior is intuitively expected since the Lucy-Richardson algorithm does not use the sparsity of the object as an optimization constraint. Besides resolution, another important difference between the two approaches is that unlike compressive sampling which can easily perform multi-layer reconstruction for sparse objects, the Lucy Richardson algorithm would need to be significantly modified to handle 3D reconstruction.

Figure 10A:
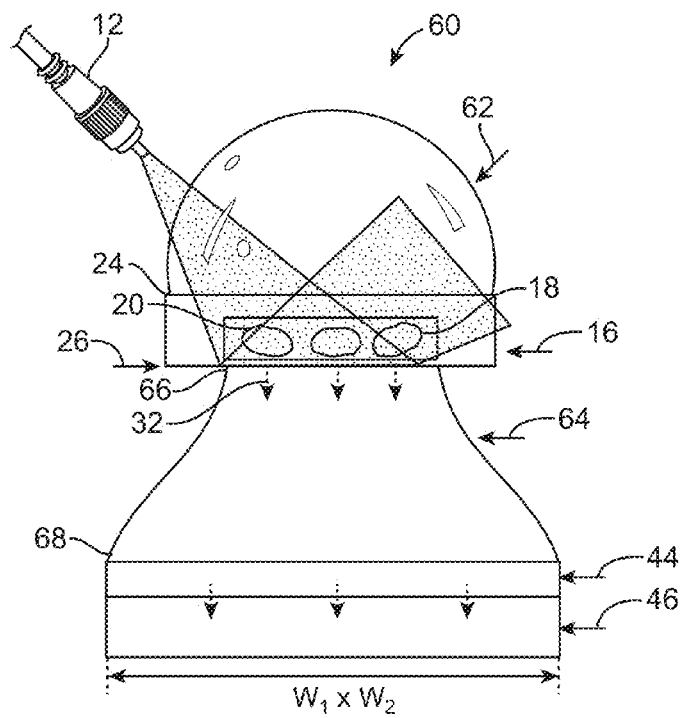
FIG. 10A is a schematic representation of an imaging device according to another embodiment. This embodiment uses a hemispheric surface instead of a prism.

FIG. 10A illustrates an imaging device 60 according to another embodiment of the invention. The imaging device 60 includes a light source 12 that serves as an excitation light source of fluorescence as previously explained herein. As seen in FIG. 10A, the light source 12 may include a fiber optic cable (e.g., multi-mode fiber optic cable), the angle of which may be adjusted to produce TIR over the entire imaging area. In the imaging device 60 of FIG. 10A, the light source 12 was provided by a Xenon lamp coupled to a monochromator such that the center wavelength was 580 nm with ~15 nm bandwidth. The sample holder 16 may include a three dimensional volume that holds the sample 18 that contains the micro-objects 20. The micro-objects 20 may include particles, cells, or the like. Like the prior embodiment, an imaging sensor array 46 is used. In this particular example, an imaging FOV of approximately 60 mm was obtained using an 11 Megapixel CCD sensor chip (KODAK, KAI-11002, 9 µm pixel size). Instead of having a prism 28, a hemispheric surface 62 is disposed above the sample holder 16 having an upper surface 24 and a lower surface 26 and is used to transmit the pumped photos to through the sample 18. The hemispheric surface 62 may be made of glass and couples the pumped excitation light from the light source 12 to the sample 18 using an index-matching gel (not shown). The orientation of fiber optic cable (light source 12) can be adjusted to produce TIL at the lower surface 26 over substantially all of the active area of the imaging sensor array 46.

The imaging device 60 also includes a tapered FOF 64 that captures fluorescent light 32 emitted from the micro-objects 20. The tapered FOF 64 has an input side 66 and an output side 68. The function of the tapered FOF 64 is that fluorescent emission from the micro-objects 20 is sampled with a dense grid of optical waveguides (~2 µm period) and is delivered to the imaging sensing array 46 with a larger grid size (~4.8 µm period) such that the relative distances in the object plane is roughly magnified by ~2.4×. An example of a commercially available tapered FOF 64 includes, for example, a tapered FOF available from Edmund Optics (NT55-134, Numerical Aperture: 1.0, Size Ratio 18:8 mm; 8.8×20×15 mm). Of course, other tapered FOFs 64 could also be used. Fluorescent light 32 emitted from the micro-objects 20 are transmitted to the input side 66 of the tapered FOF 64 and exit the tapered FOF 64 via the output side 68. An absorption filter 44 is interposed between the tapered FOF 64 and the imaging sensor array 26.

The absorption filter 44 can be manufactured by coating 30 µm thick glass substrates with a dye. This fabrication process starts with dissolving Orasol dyes in cyclopentanone solvent and adding KMPR 1005 Photoresist (~0.4 g ml$^{-1}$ dye concentration), after which the excess dye material in the mixture is removed using a 0.45 µm diameter porous filter. The raw solution is then processed by spin coating for 20 seconds at 2000 rpm, baking for 300 seconds at 100° C., flood exposure at 13 mW/cm$^2$ for 35 seconds, and finally baking for another 120 seconds at 100° C. One of these fabricated absorption filters 44 can then be gently placed on the imaging sensor array 46 with a vacuum pen. A housing (not shown) may be formed to cover the optical components of the imaging device 60. Blocking unwanted light is important to decrease the leakage from excitation or ambient light, which can decrease the image contrast.

Referring back to FIG. 3A, raw images can be transferred to a computer 50 for processing. Processing can include subjecting the raw image frames 48 to a compressive decoding algorithm 52 as described above in detail. The compressively decoded image frames 54 can then be displayed on a display 56 or subject to additional processing. Raw image frames 48 as well is implementation of the compressive decoding algorithm 52 may be run using conventional laboratory processing software such as, for instance, Labview.

Figure 10B:
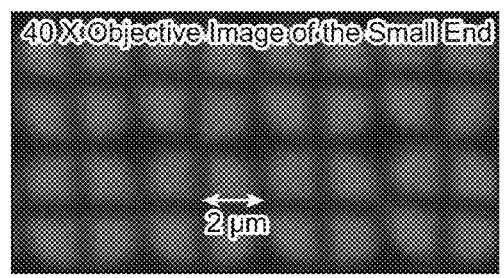
FIG. 10B is a microscopic image (40× objective) of the input side of the tapered FOF.
Figure 10C:
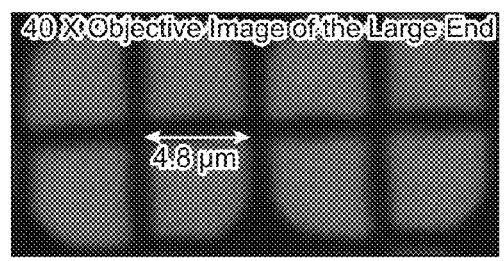
FIG. 10C is a microscopic image (40× objective) of the output side of the tapered FOF.

FIGS. 10A and 10B illustrate microscope (40× objective lens) images of the input side 66 and output side 68 of the tapered FOF 64, respectively. A main function of the tapered FOF 64 can also be understood from the perspective of PSF engineering, i.e., for a given pixel size at the imaging sensor array 46, through the use of the FOF 64, an optimum PSF is created. Tapering off the FOF 64 as shown in FIG. 10A adds another advantage through image magnification such that more pixels can now detect the lensfree emission of the micro-objects 20 without sacrificing the detection SNR or without introducing spatial aberrations within the large imaging FOV. Besides PSF engineering, another valuable function of the tapered FOF 64 is thermal isolation of the micro-objects 20 from the imaging sensor array 46 and the reader circuit such that operating temperatures within the sample holder 16 can be better controlled.

Experimental Results

Second Embodiment

The imaging device 60 as illustrated in FIG. 10A was tested by imaging 4 and 2 µm diameter fluorescent particles as well as *Giardia Muris* cysts. As in the prior embodiment, raw image frames 48 reflecting the lensfree fluorescent image of the micro-objects 20 were detected at the imaging sensor array 46. These raw image frames 48 are then subject to a compressive decoding algorithm 52 as illustrated in FIGS. 3A and 3B, to yield decoded image frames 54.

Fluorescent beads with 4 µm and 2 µm diameters (excitation 580 nm/emission 605 nm) were purchased from Invitrogen (Carlsbad, Calif.). The stock solution was diluted 4000 times with DI water in small aliquots. Then, using a micropipette, the bead solution (~10 µl) is transferred onto a disposable glass substrate (thickness: ~30-100 µm) and is sandwiched using another glass substrate before being imaged using the imaging device 60.

*Giardia Muris* cysts were purchased from Waterborne Inc. (New Orleans, La., USA). The stock solution of these cysts has a concentration of ~5×10$^6$ parasites/mL. To avoid the dynamic motion of the parasites, they were fixed in 5% Formalin/PBS at pH 7.4/0.01% Tween-20. A small amount of this solution (e.g. 100-200 µL) was centrifuged and re-suspended in the form of PBS suspension. For the labeling dye, 1 mM SYTO®64 nucleic acid dye was used with the mixing ratio of 5 µL of dye and 100 µL parasite-consisting suspensions. Once prepared, this mixture was incubated in dark environment for ~30 min. Just after activation of dye labeling within the parasite body (Emission peak wavelength: 619 nm), the unbound dyes (which might potentially introduce unwanted background) were removed by another centrifuging and re-suspension in PBS. The final sample solution was then placed between two glass slides for wide-field lensfree imaging on the imaging device 60.

Similar to the first embodiment, compressive sampling based decoding was used to partially undo the effect of diffraction. In this method, the point-spread-function of the lensfree imaging system was measured using small fluorescent particles (e.g., ~2 µm diameter). Several lensfree fluorescent spots of isolated particles are aligned with respect to each other and are then averaged to yield the lensfree fluorescent point-spread-function of the imaging device 60. Based on the observed psf, for any arbitrary distribution of fluorescent point sources at the object plane, one can calculate the expected lensfree fluorescent pattern that is to be sampled at the detector plane. To decode a given lensfree fluorescent image, the compressive decoding algorithm 52 iteratively minimizes (using truncated Newton interior-point method as described above) a cost function that is defined by $l_1$-regularized least square error between the calculated lensfree fluorescent pattern and the measured one at the imaging sensor array 46. This entire optimization process is based on sparsity of the fluorescent distribution at the object plane and it typically converges after ~40-60 iterations taking ~0.5-2 minutes for e.g., the regions of interest using a 3.2 GHz processor (INTEL CORE i5 CPU 650). As a result of this compressive decoding process, the resolving power of the imaging device 60 significantly increases achieving <4 µm resolution over a wide field-of-view of ~60 mm$^2$.

FIGS. 11A-11D illustrate a panel of images of 4 µm sized micro-objects 20. FIG. 11A illustrates a wide-filed lensfree image of the entire imaging FOV (~60 mm$^2$) of the imaging device 60 of FIG. 10A. FIG. 11B illustrates the raw image frame 48 of a portion of the lensfree fluorescent image. FIG. 11C illustrates the decoded image frame 54 after compressive decoding. FIG. 11D illustrates microscopic images of the same micro-objects 20 (4 µm diameter) using a conventional lens-based fluorescent microscope (10× objective lens, NA=0.25).

To quantify the resolution of the imaging device 60, as seen in FIGS. 12A-12L the smaller regions of interest where the fluorescent particles (2 µm diameter) were close to each other were analyzed. FIGS. 12C, 12F, 12I, 12L illustrate brightfield microscope images of these fluorescent particles which act as a reference in terms of the distances (d) between particles. FIGS. 12A, 12D, 12G, 12J illustrate the raw lensfree fluorescent images (which are pixelated) for the same particles. FIGS. 12B, 12E, 12H, 12K illustrate the CS decoded versions of the respective raw image frames 48 to validate the resolution. Note that unlike conventional lens-based microscopy, objects separated by <15 µm partially overlap with each other at the detector plane due to unavoidable diffraction occurring in this lensfree platform. FIGS. 12B, 12E, 12H, 12K demonstrate that one can resolve closely spaced fluorescent particles from each other, achieving a lensfree spatial resolution of <4 µm. Considering that the pixel size at the CCD chip of this lensfree on-chip imager is 9 µm, a resolution of <4 µm is quite significant.

Figures 13A, 13B, 13C:
FIG. 13A illustrates the raw lensfree fluorescent image frame 48 of *Giardia Muris* cysts.
FIG. 13B illustrates the decoded image frame 54 of the raw image frame 48 of FIG. 13A.
FIG. 13C illustrates a conventional microscope image (10×) of the same FOV.

The performance of the imagine device 60 has also been validated by imaging labeled *Giardia Muris* cysts as illustrated in FIGS. 13A, 13B, and 13C. When combined with its large FOV within a compact on-chip platform, these results could be especially important for rapid screening of waterborne parasites in field settings. FIG. 13A illustrates the raw lensfree fluorescent image frame 48 of *Giardia Muris* cysts. FIG. 13B illustrates the decoded image frame 54 of the raw image frame 48 of FIG. 13A. FIG. 13C illustrates a conventional microscope image (10×) of the same FOV.

A function of the tapered FOF 64 the imaging device 60 is that the fluorescent emission from the micro-objects 20 is sampled with a dense grid of optical waveguides (~2 µm period) and is delivered to the imaging sensor array 46 with a larger grid (~4.8 µm period) such that the relative distances in the object plane is roughly magnified by ~2.4×. While this magnification is an important parameter for spatial resolution, there are other factors that significantly affect the achievable resolution in this platform.

Detection Signal-to-Noise Ratio (SNR)

This parameter is governed by several factors, ranging from noise floor of the sensor, faceplate-to-sensor and object-to-faceplate distances, the numerical aperture of the faceplate, as well as the emission intensity of the objects and the strength of the dark-field background. In principle, if the SNR of the raw fluorescent images is very high, the resolution of the compressively decoded images can become independent of the magnification of the faceplate taper, and can in theory approach sub-micron levels. Therefore, active cooling of the opto-electronic sensor array is an important route that can be used to further improve lensfree resolution without a trade-off in our imaging FOV. The fact that the thickness of the tapered FOF 64 is >1-2 cm can also thermally isolate the samples from the sensor chip, helping to implement active cooling of the sensor without a damage to the samples. Generally, the thickness of the tapered FOF 64 within the range of about 100 µm to about 5 cm will suffice. Such an increased digital SNR would also increase the detection numerical aperture of our platform, such that more of the oblique fluorescent rays can now be detected above the noise floor of the sensor. Therefore under improved SNR levels, the detection numerical aperture will be ultimately limited by the numerical aperture of the tapered FOF 64, which in this experimental set-up was ~1.

Other key parameters that set the detection SNR are the faceplate-to-sensor and object-to-faceplate distances. The object-to-faceplate vertical distance can be minimized with a contact configuration (i.e., ~5-10 µm). However, the faceplate-to-sensor vertical distance will have to be limited with the thickness of the absorption filter 44 which can get as small as ~20-30 µm. One other parameter that will directly determine the detection SNR in the imaging device 60 is the fluorescent emission intensity of the samples (compared to the background) which is mostly determined by the quantum efficiency of labeling dyes, excitation power and wavelength, as well as the labeling efficiency of the sample. The digital SNR of the resulting images is one of the most important factors that influence the spatial resolution of the imaging device 60, which can potentially achieve sub-micron resolution by further systematic improvements in the achievable SNR.

Lensfree Point-Spread Function (PSF)

The lensfree PSF of the imaging device 60 is defined the 2D spatial function that represents the fluorescent emission pattern of a point source at the object plane, before being sampled by the imaging sensor array 46 at the detector plane. Under a strong detection SNR and a large pixel size at the imaging sensor array 46 (as we typically employ, e.g., ~9 µm), the narrowest lensfree PSF is not necessarily the best route for improving CS decoded resolution. To better understand this argument, assume that the spatial width of the lensfree PSF is hypothetically made smaller than the large pixel size at the imaging sensor array 46. In this case, two fluorescent points that are close to each other at the sub-pixel level would both contribute to a single pixel, which makes it impossible to resolve them no matter what type of digital decoder is used. Simply put, infinitely many different combinations of these two point sources within the same pixel would yield the same signal, making decoding at the sub-pixel level physically impossible.

However, for the same pixel size and digital SNR at the imaging sensor array 46, if this time the width of the lensfree PSF is increased (which could be achieved by e.g., slightly increasing the vertical distance of the object plane from the sensor surface), then decoding of these sub-pixel separated objects would be feasible since several different pixels (dictated by the practical width of the PSF) can now detect weighted sums of these two closely spaced point sources. This conclusion is true as long as the detection SNR does not degrade significantly (getting close to the noise floor of the sensor) due to spatial broadening.

In other words, for a given large pixel size at the imaging sensor array 46, after a certain PSF width is reached, a further increase in its width might start to practically reduce the detection SNR due to signal spreading, and this would set the boundary for the optimum PSF, which is entirely dictated by the pixel size at the imaging sensor array 46 and the noise performance of lensfree platform. As stated above, one way to avoid this is to slightly increase the vertical distance of the object plane from the surface of the imaging sensor array 46.

One main function of the tapered FOF 64 in lensfree fluorescent on-chip imaging can also be understood from the perspective of PSF engineering, i.e., for a given pixel size at the sensor chip, through the use of a faceplate, an optimum PSF is created. The tapered configuration of FOF 64 adds another advantage through image magnification such that more pixels can now detect the lensfree emission of the objects without sacrificing the detection SNR or without introducing spatial aberrations within the large imaging FOV.

While embodiments of the present invention have been shown and described, various modifications may be made without departing from the scope of the present invention. The invention, therefore, should not be limited, except to the following claims, and their equivalents.

What is claimed is:
1. An imaging device comprising:
a sample holder configured to hold a sample, the sample holder having a lower surface and comprising a plurality of micro-channels located at different vertical positions;
a hemispheric surface disposed adjacent the sample holder on a side opposite the lower surface of the sample holder;

a light source configured to illuminate the sample via the hemispheric surface, wherein substantially all of the light is subject to total internal reflection at the lower surface of the sample holder;

a fiber optic array disposed adjacent to the lower surface of the sample holder, the fiber optic array having an input side and an output side, wherein the input side of the fiber optic array has higher density of fiber optic waveguides compared to density of fiber optic waveguides at the output side;

an imaging sensor array disposed adjacent to the output side of the fiber optic array, the imaging sensor array outputting image frames of the sample; and a processor configured to compressively decode the image frames from the imaging sensor array and output decoded image frames having a higher resolution.

2. The imaging device of claim 1, further comprising an absorption filter interposed between the output side of the fiber optic array and the imaging sensor array.

3. The imaging device of claim 1 wherein the density of fiber optic waveguides at the input side of the fiber optic array is more than five times greater than the density of the fiber optic waveguides at the output side of the fiber optic array.

4. The imaging device of claim 1, wherein the fiber optic array has a thickness within the range of about 100 µm to about 5 cm.

5. A method of imaging a sample comprising:

illuminating the sample contained in a sample holder comprising a plurality of micro-channels located at different vertical positions with fluorescent excitation radiation passing through a hemispheric surface prior to illuminating the sample, wherein substantially all of the fluorescent excitation radiation is subject to total internal reflection at a lower surface of the sample holder and fluorescent emission radiation from the sample exits the sample holder;

transferring the fluorescent emission radiation exiting the sample holder to an imaging sensor array via a fiber optic array interposed between the lower surface of the sample holder and a surface of the imaging sensor array, and wherein an input side of the fiber optic array has higher density of fiber optic waveguides compared to the density of fiber optic waveguides at an output side;

acquiring image frames of the fluorescent emission radiation exiting the output side of the fiber optic array with the imaging sensor array; and subjecting the acquired image frames to compressive decoding to produce decoded image frames having a higher resolution.

6. The method of claim 5, wherein the sample comprises a plurality of cells.

7. The method of claim 5, further comprising identifying one or more target cells contained within the plurality of cells.

8. The method of claim 5, wherein a first air gap separates the lower surface of the sample holder from the input side of the fiber optic array and a second air gap separates the output side of the fiber optic array and the surface of the imaging sensor array.

9. The method of claim 8, wherein the first and second air gaps between the fiber optic array and the sample holder and imaging sensor are within the range of about 1 to about 500 µm.

* * * * *